US012002554B2

(12) United States Patent
Hassett

(10) Patent No.: US 12,002,554 B2
(45) Date of Patent: *Jun. 4, 2024

(54) MANAGEMENT AND TRACKING SOLUTION FOR SPECIFIC PATIENT CONSENT ATTRIBUTES AND PERMISSIONS

(71) Applicant: IQVIA Inc., Durham, NC (US)

(72) Inventor: Peter Hassett, Danbury, CT (US)

(73) Assignee: IQVIA Inc., Durham, NC (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/710,090

(22) Filed: Mar. 31, 2022

(65) Prior Publication Data
US 2022/0223238 A1 Jul. 14, 2022

Related U.S. Application Data

(63) Continuation of application No. 16/280,750, filed on Feb. 20, 2019, now Pat. No. 11,309,065.

(51) Int. Cl.
G06F 40/197 (2020.01)
G06F 40/174 (2020.01)
G16H 10/20 (2018.01)
G06F 3/0482 (2013.01)

(52) U.S. Cl.
CPC .......... *G16H 10/20* (2018.01); *G06F 40/174* (2020.01); *G06F 40/197* (2020.01); *G06F 3/0482* (2013.01)

(58) Field of Classification Search
None
See application file for complete search history.

(56) References Cited

U.S. PATENT DOCUMENTS

| | | | |
|---|---|---|---|
| 9,378,205 B1* | 6/2016 | Schmidt | G06F 16/28 |
| 10,325,079 B1* | 6/2019 | Vukich | H04L 9/3239 |
| 2002/0116227 A1 | 8/2002 | Dick | |
| 2003/0204418 A1 | 10/2003 | Ledley | |

(Continued)

OTHER PUBLICATIONS

Obeid et al. "Development of an electronic research permissions management system to enhance informed consents and capture research authorizations data." AMIA Summits on Translational Science Proceedings 2013 (2013): 189. (Year: 2013).*

(Continued)

*Primary Examiner* — Frank D Mills
(74) *Attorney, Agent, or Firm* — John Maldjian, Esq.; David L. D'Amato, Esq.; Stevens & Lee PC

(57) ABSTRACT

A method of managing consent using a computing device, the consent is given by a subject to one or more events in one or more studies, wherein the consent and the plurality of activities are changeable, the method including: authoring one or more first data forms describing the one or more events and one or more selections responsive to the one or more events; authoring, for each of the plurality of subjects, one or more second data forms including description of a plurality of preferences; forming, for a first of the plurality of subjects, an Informed Consent Forms document by combining the one or more first data forms of a first of the one or more studies and one or more second data forms for the first subject; and generating a manifest indicating the one or more events in the first study to which the first subject has granted consent.

20 Claims, 4 Drawing Sheets

(56) References Cited

U.S. PATENT DOCUMENTS

| | | |
|---|---|---|
| 2003/0033168 A1 | 11/2003 | Califano |
| 2003/0212578 A1 | 11/2003 | Link |
| 2004/0133454 A1 | 7/2004 | Desio |
| 2006/0178913 A1 | 8/2006 | Lara |
| 2006/0282292 A1 | 12/2006 | Brink |
| 2008/0300915 A1* | 12/2008 | Molmenti ............. G16H 10/60 705/2 |
| 2009/0164245 A1 | 6/2009 | Toleti |
| 2009/0182579 A1 | 7/2009 | Liu |
| 2010/0094650 A1* | 4/2010 | Tran ..................... G16H 40/20 705/2 |
| 2010/0299159 A1 | 11/2010 | Califano et al. |
| 2011/0166873 A1* | 7/2011 | Griffin ................. G16H 10/60 705/2 |
| 2012/0151557 A1* | 6/2012 | Ahmed ............... G06F 21/6218 715/764 |
| 2012/0323589 A1* | 12/2012 | Udani .................... G06Q 50/18 707/769 |
| 2012/0323590 A1* | 12/2012 | Udani .................. G06Q 10/103 348/40 |
| 2012/0323796 A1* | 12/2012 | Udani .................... G16H 10/20 705/80 |
| 2013/0054272 A1* | 2/2013 | Rangadass ............ G16H 10/60 705/3 |
| 2013/0173642 A1* | 7/2013 | Oliver ................... G06F 40/20 707/756 |
| 2014/0108043 A1* | 4/2014 | Ach ...................... G16H 10/60 705/3 |
| 2014/0108054 A1 | 4/2014 | Udani |
| 2014/0188512 A1 | 7/2014 | Parker |
| 2016/0078196 A1* | 3/2016 | Malbon, Jr. .......... G16H 10/40 705/3 |
| 2017/0024547 A1* | 1/2017 | Bidani .................. G16H 10/20 |
| 2017/0154166 A1 | 6/2017 | Klein |
| 2017/0316163 A1 | 11/2017 | Wall Warner |
| 2018/0082024 A1* | 3/2018 | Curbera ................ G16H 40/63 |
| 2018/0336406 A1 | 11/2018 | Shimazaki |
| 2018/0373891 A1* | 12/2018 | Barday .................. G06F 15/76 |
| 2019/0005210 A1* | 1/2019 | Wiederspohn .......... G06F 21/31 |
| 2019/0019574 A1* | 1/2019 | Byrnes .................. G16H 70/20 |
| 2019/0179490 A1* | 6/2019 | Barday .................. G06F 3/0484 |
| 2019/0180012 A1* | 6/2019 | Barday ............... G06F 21/6245 |
| 2019/0180051 A1* | 6/2019 | Barday ............... G06F 11/3065 |
| 2019/0180054 A1* | 6/2019 | Barday .................. G06F 15/76 |
| 2019/0215344 A1* | 7/2019 | Barday ............... H04L 63/0407 |
| 2019/0259476 A1* | 8/2019 | Armijos ........... G06F 16/90335 |
| 2020/0153835 A1* | 5/2020 | Jacobs ................ H04L 63/0815 |

OTHER PUBLICATIONS

European Search Report dated Jun. 24, 2020, issued in connection with corresponding European Patent Application No. 20158140.2 (11 pages total).

Bickmore, Timothy, Dina Utami, Shuo Zhou, Candace Sidner, Lisa Quintiliani, and Michael K. Paasche-Orlow. "Automated explanation of research informed consent by virtual agents." In International Conference on Intelligent Virtual Agents, pp. 260-269. Springer, Chant', 2015. (Year: 2015) (10 pages total).

Fatema, Kaniz, Ensar Hadziselimovic, Harshvardhan J. Pandit, Christophe Debruyne, Dave Lewis, and Declan O'Sullivan. "Compliance through Informed Consent: Semantic Based Consent Permission and Data Management Model." In PrivOn@ ISWC. 2017. (Year: 2017) (16 pages total).

European Office Action dated Apr. 6, 2023; issued in connection with corresponding European Application No. 20158140.2 (7 pages total).

Canadian Office Action dated Jan. 27, 2023; issued in connection with corresponding Canadian Application No. 3,069,735 (5 pages total).

\* cited by examiner

E-consent System

200

Retention policy of samples after withdrawal (ICF Block 4)

| Destroy samples | ⇕ |

Samples types that should be destroyed after withdrawal

| Please specify | ⇕ |

| Blood samples | |

Data usage after withdrawal (ICF Block 8)

| Data will Not continue to be used | ⇕ |

Sample Storage and Future Use (ICF Block 4)

Sample Purpose

| Specified | ⇕ |

Fig. 2

MANAGEMENT AND TRACKING SOLUTION FOR SPECIFIC PATIENT CONSENT ATTRIBUTES AND PERMISSIONS

CROSS-REFERENCE TO RELATED APPLICATION

This application is a continuation of U.S. Ser. No. 16/280,750, filed Feb. 20, 2019, entitled "MANAGEMENT AND TRACKING SOLUTION FOR SPECIFIC PATIENT CONSENT ATTRIBUTES AND PERMISSION", now U.S. Pat. No. 11,309,065, which is incorporated by reference herein in its entirety.

FIELD OF INVENTION

The present system relates to management of patient consent.

BACKGROUND OF INVENTION

At present, it is impossible to determine for large datasets, i.e., at scale, and without extreme manual effort, high error rates, and unnecessary access to Patient Identifying Information, which patients and subjects of a clinical research or study have consented to which procedures, granted which permissions, offered which biological samples/specimens, etc. This task may involve reading the patients'/subjects' Informed Consent Forms (ICF) document that include the patients'/subjects' signatures. Such ICF document may include, e.g., 30-pages.

Moreover, biological samples/specimens that may be gained through specific clinical research or study, currently have a limited value. This is because such biological samples/specimens are collected for a specific context of that clinical research or study. Reuse of the biological samples/specimens, which increases their value and lowers the cost of the clinical research or studies is limited because of existing difficulties in a. identifying the patients or subjects from whom the biological samples/specimens were taken and to whom they belong;
   b. determining permissions granted by the patients or subjects and pertaining to the biological samples/specimens;
   c. asking the patients or subjects for additional permissions to their biological samples/specimens, if and when the additional permissions become necessary;
   d. failure to ask the patients or subjects to grant proper use permissions of the biological samples/specimens in the first place; and
   e. inconsistencies in what the permissions for the additional use of the biological samples/specimens have been granted in the text of the ICF document.

Manual tracking of patients' or subjects' consent permissions on a document-level, sometimes occurs, but it is inconsistent, unreliable, and labor-intensive. When information regarding the patients' or subjects' consent permissions is required, medical staff often refers to, and reads a full, signed ICF document to discern specific permissions for specific biological samples/specimens and/or procedures. Phrased differently, reading and discerning of a full, signed ICF document by a person is required for different medical clinical research or studies at different sites, and in different languages. This makes computer based pattern analysis difficult and sometimes impossible.

Worse, where biological samples/specimens collected through the clinical research or studies are concerned, sponsors of such studies and medical personnel often have no way of understanding annotations on the signed ICF documents. This causes the biological samples/specimens to be misidentified, or at least not clearly identified or not being associated with the patient or subject. Importantly, use of the biological samples/specimens, without clearly identifying the patient or subject who granted the consent is not permissible in the clinical research or studies. At present, verifying patient or subject consent is not possible other than by manually reading the signed ICF

DOCUMENTS

Some existing approaches address tracking of the patient consent through the use of manual data tracking in spreadsheets. Also cross-referencing biological samples/specimens with subjects IDs with their signed consents at medical and clinical research sites. However, such attempts are inadequate. They rely on re-identification of the subjects to understand their consent. These approaches lack structured data and do not provide scalability, which leads to a loss of the biological samples/specimens to destruction due to insufficient documentation. Further, these approaches are usually restricted to the document level, and do not encompass interactions with the medical and clinical research sites and patients.

SUMMARY OF INVENTION

It is an object of the present inventive system to overcome disadvantages and/or make improvements in the prior art;

It is an object of the inventive system to enable controls for defining of consent attributes as structured and quantifiable data at medical and clinical research site-level, Informed Consent Forms document-level, and patient-level;

It is still another object of the present inventive system to enable storage of these attributes as metadata in variable contexts, e.g., studies, documents, and patients;

It is another object of the present inventive system to make this information available to other systems; and It is yet another object of the present inventive system to enable the concatenation/continual updating of these metadata over time for easy reliable access. As will be described below, the inventive system enables (a) direct and seamless consent document-authoring; (b) patient electronic consent (e-consent) processes/lifecycles; (c) progressive updating of e-consent data responsive to withdrawal of consent, re-consent, etc.; (d) capturing patient related attribute information at the moment of consent that is not based on later manual data repatriation; (e) user-driven declaration/configuration of form by administrators and content engineers; and (f) exhaustive query ability of subject/sample consent attributes at enterprise scale, i.e., hundreds of thousands of samples/subjects.

Provided is a method of managing consent using a computing device, the consent is given by a subject of a plurality of subjects to one or more events in one or more studies, wherein the consent and the plurality of activities are changeable, the method including: authoring one or more first data forms describing the one or more events and one or more selections responsive to the one or more events; authoring, for each of the plurality of subjects, one or more second data forms including description of a plurality of preferences; forming, for a first of the plurality of subjects, an Informed Consent Forms document by combining the one or more first data forms of a first of the one or more studies and one or more second data forms for the first subject; and generating a manifest indicating the one or more events in the first study to which the first subject has granted consent.

BRIEF DESCRIPTION OF DRAWINGS

The invention is explained in further detail, and by way of example, with reference to the accompanying drawings wherein:

FIG. 2 is a diagram illustrating a user interface used on the computing device to create data forms that describe the attributes of the study in accordance with art embodiment of the present inventive system;

DETAILED DESCRIPTION OF INVENTION

Figure 1:
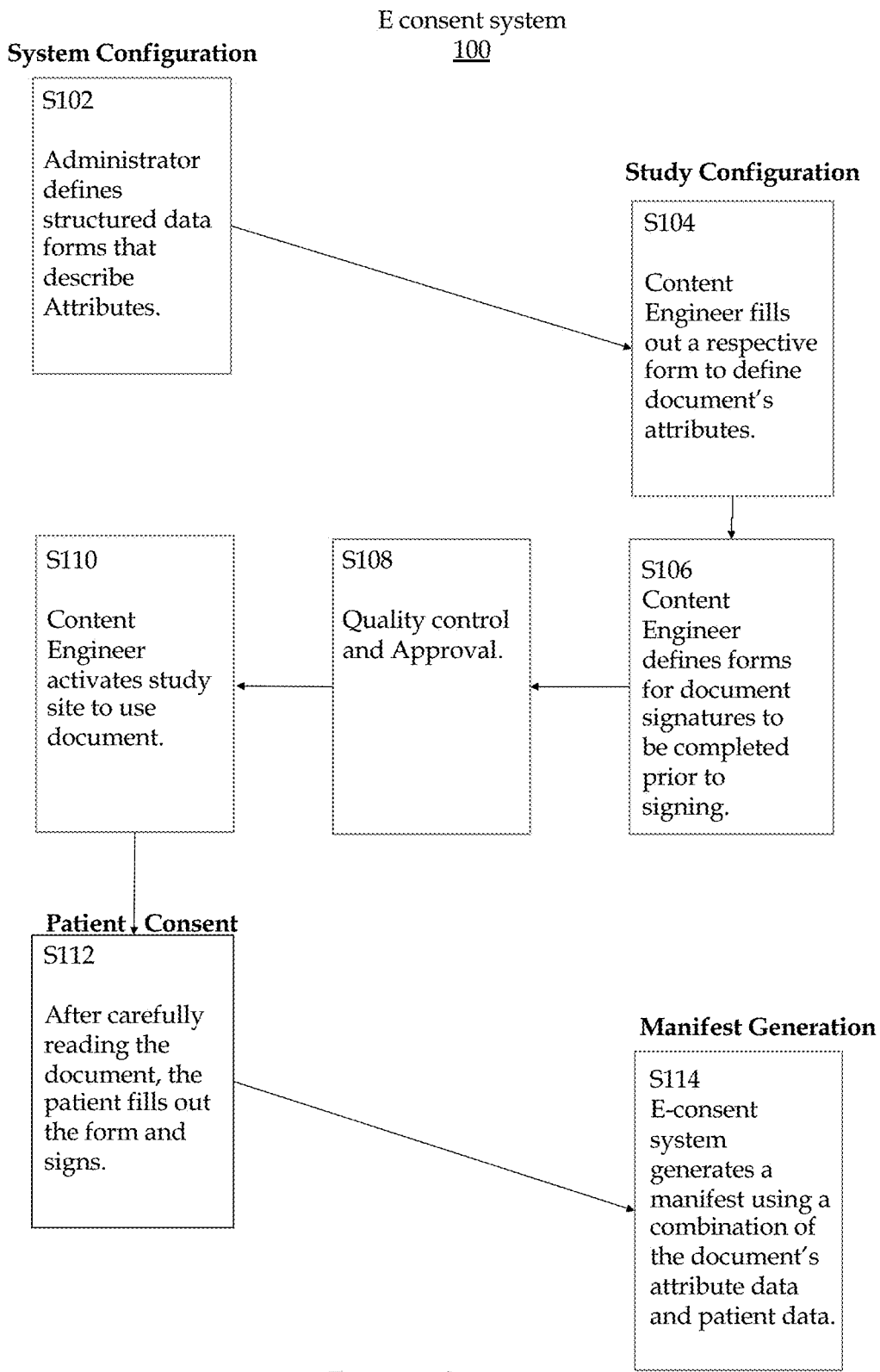
FIG. 1 is a diagram illustrating workflow of the present inventive system from inception to generation of the manifest on a computing device in accordance with an embodiment of the present inventive system.

The following are descriptions of illustrative embodiments that when taken in conjunction with the following drawings will demonstrate the above noted features and advantages, as well as further ones. In the following description, for purposes of explanation rather than limitation, illustrative details are set forth such as architecture, interfaces, techniques, element attributes, etc. However, it will be apparent to those of ordinary skill in the art that other embodiments that depart from these details would still be understood to be within the scope of the appended claims. Moreover, for the purpose of clarity, detailed descriptions of well-known devices, tools, techniques, and methods are omitted so as not to obscure the description of the present inventive system. It should be expressly understood that the drawings are included for illustrative purposes and do not represent the scope of the present inventive system. In the accompanying drawings, like reference numbers in different drawings may designate similar elements.

The present inventive system introduces a top-level Informed Consent Form (ICF) document having a configuration that allows for standardization of fields across many documents relating to handling and utilization of biological samples/specimens for various clinical research or studies. A sponsor of each clinical research or study may design a standard form to describe attributes that will be included in each ICF document. The attributes are structured data describing various aspects of the clinical research or studies and the meaning of consent, precisely to what the consent is being given. Thus, the ICF document-level attributes may be declared during the ICF document-authoring lifecycle, rather than retrospectively.

The attributes may be stored in context of software objects, e.g., ICF documents' attributes and a patients' data document attributes, rather than in manually managed, disassociated spreadsheets. Concatenation of the ICF document and the patient data document may allow for generation of a manifest of attributes, i.e., permissions, that is not achievable outside of consent without duplicate data entry.

The inventive system provides reliable metadata in the ICF document, accommodates explicit requests for permissions given in the ICF document, and enables a novel tracking of answers given in the context of an original patient consent. This results in empowerment of known and potential users of the biological samples/specimens to determine both the specifics and patterns of consent in a quantifiable way with low error, minimal effort, and no unnecessary access to Patient Identification Information (PII). This greatly increases the research value of the biological samples/specimens because the inventive system enables their reuse while providing reliable bookkeeping of patient consent information. This ability to reuse the biological samples/specimens and reliability of the patient consent information will lower barriers to entry for research.

FIG. 1 illustrates inventive e-consent system 100 that aims to define structured attribute describing data forms describing individual clinical research or studies for which the biological samples/specimens are being procured. The data forms define the attributes of the clinical research or studies.

Thus, the purpose of the inventive e-consent system 100 may be achieved in about four stages. In the first stage, a system configuration stage, at step S102 someone in a position of responsibility, e.g., an administrator of the e-consent system 100, defines or structures the data forms of the ICF document that describe the attributes of the clinical research or study. These attributes may include type, purpose and descriptions of the biological samples/specimens; intended retention or duration for storage of the biological samples/specimens; intent to reuse of the biological samples/specimens and etc. The values of the attributes can be static, e.g. expire at end of study, or dynamic, e.g. 3 years+date of consent.

In the second stage, a study configuration stage, at step S104, again someone in a position of responsibility, e.g., the administrator or a content engineer, selects and identifies the characteristics of structured data forms to be filed and signed by patients or study participants. The characteristics indicate the patients' or study participants' consent to various medical procedures, giving of the biological samples/specimens, and use of the biological samples/specimens in specified and/or unspecified studies. The structured data forms with the selected characteristics should be designed to provide transparency, efficiency, and reliability in assuring proper consent.

As further illustrated, at step S106, forms that require signatures and are to be completed prior to signing are defined. At step S108, quality of the forms is examined and approved. Which is followed at step S110 by the document being activated for use on the clinical research or study website accessible to computer devices via a network, e.g., the Internet.

As stated above, once the questions or descriptions are answered and filled in, e.g., by the administrator, they become the properties, i.e., the attributes of the document being authored. Later, when the patient signs the ICF document, that ICF document's attributes are conferred to the signing patient. And the administrator can look up the attributes of each signing patient's ICF document.

In the third stage, a patient consent stage, at step S112, after carefully reading the document information, the patient fills out all the necessary fields in the data form, e.g., date of birth, and signs. After the signature is obtained, at step S114, e-consent system 100 generates a manifest using a combination of the document's attribute data and patient data.

As illustrated in FIG. 2, the administrator creates the data forms including questions to define the attributes of the clinical research or study. The questions and descriptions, as exemplary and non-exhaustively illustrated in FIG. 2, may pertain e.g., to (1) the biological samples/specimens retention policy after withdrawal of consent; (2) the biological samples/specimens destruction policy after withdrawal of consent; (3) usage of data learned about the biological samples/specimens after withdrawal of consent; and (4) the purpose for the biological samples/specimens. Data entry fields, e.g., drop down fields including possible answers pertaining to the particular clinical research or study will be provided by the administrator including, for example, various durations for retention of the biological samples/specimens or their destruction. Also corresponding data entry fields may be provided for typed answers.

The data forms, like the one illustrated in FIG. 2, are created and published using an inventive form-builder application executing on a general purpose computer. The form-builder application enables the administrator to create the data forms by adding forms' fields and defining the fields' rules. The fields are then filled out and the forms signed. The administrator defines a standard form, which when filled out describes the metadata of a document. The document is filled out to accommodate specific clinical research or studies by the administrator itself or another authority. Then the document is signed by the patient who consents to participate in the clinical research or studies as outlined in the document. Once the document is signed, the form-builder application associates the patient with the metadata of the document.

Also, once published, the data forms can be revised and previewed. When the data forms are created and revised the administrator, or another responsible party, chooses which data form is to be applied to the ICF document. Then, before publishing, when all required fields in the data form are fill out the respective attributes may be generated.

An example of the generated attributes of the ICF document may look as follows:

```
{
  "Attributes": [{
    "name": "Retention policy of samples after withdrawal (ICF Block 4)", "value": "Destroy samples"
  }, {
    "name": "Samples types that should be destroyed after withdrawal",
    "value": "NA"
  }, {
    "name": "Data usage after withdrawal (ICF Block 8)",
    "value": "Data will continue to be used"
  }, {
    "name": "Sample Purpose",
    "value": "Specified"
  }, {
    "name": "Sample Optional?",
    "value": "Yes"
  }, {
    "name": "Storage duration of samples",
    "value": "End of study"
  }]
}
```

Importantly, the attribute data of the ICF document may be stored as a property of each medical and clinical research site document-version. The attribute data of the ICF document may be changed with each version or revision of the ICF document. The version is conferred on the ICF document when a patient signs the document thereby conferring consent. Also, when the patient signs, the attribute data for that version of the ICF document is conferred to the patient, thereby forming the manifest of the patient's consent.

To be clear, the ICF document may have many versions, and each version may include changes to the document's content (e.g. updating risks), version information (e.g. from version 1 to version 2), and other metadata (e.g. attributes). When the patient signs a "main consent form" for a particular study, the inventive system possesses much more information than simply which document was signed. The information includes the version, language, content, and attributes of the form. Change management, i.e., version control for the ICF documents allows for protocol amendments in the clinical research or studies.

Where there are multiple ICF documents, each may contain different attributes. The attribute data of the many documents can be quarried to find all ICF documents which attributes do not limit some particular use of the biological samples/specimens in previously unspecified research. Moreover, report may be run to list ICF documents having particular attributes and printed, displayed or exported in various formats, e.g., simple file format CSV where one row per ICF document-version using that form and columns for each value that can be represented tabularly.

Table 1 illustrates an example of a report on the patients and their attributes vis a vis the ICF documents the patients signed. In this example, the patients consented to study ABCD1234 in April. Later, some of the patients re-consented to an amended ICF document with changes to attributes. (This is illustrative of how document-versions can contain changes from prior versions.) The specific fields will vary based on how attribute related fields are defined in the forms (i.e., per study sponsor) and how the ICF document attributes are specified (i.e. per study).

TABLE 1

| Study ID | Subject ID | Initial Consent Date | Most Recent Consent Date | Current Consent Status | sample-type | sample-retention-period-years | sample-reuse-permissions |
|---|---|---|---|---|---|---|---|
| ABCD1234 | S00001 | Apr. 12, 2018 | Apr. 12, 2018 | Needs to reconsent | blood | 3 | this-condition |
| ABCD1234 | S00002 | Apr. 13, 2018 | Nov. 14, 2018 | Consented | blood | 2 | all-purposes |
| ABCD1234 | S00003 | Apr. 14, 2018 | Apr. 14, 2018 | Needs to reconsent | blood | 2 | this-condition |
| ABCD1234 | S00004 | Apr. 15, 2018 | Apr. 15, 2018 | Needs to reconsent | blood | 2 | this-condition |
| ABCD1234 | S00005 | Apr. 16, 2018 | Apr. 16, 2018 | Needs to reconsent | blood | 2 | this-condition |
| ABCD1234 | S00006 | Apr. 17, 2018 | Nov. 14, 2018 | Consented | blood | 3 | all-purposes |
| ABCD1234 | S00007 | Apr. 18, 2018 | Nov. 14, 2018 | Consented | blood | 3 | all-purposes |
| ABCD1234 | S00008 | Apr. 19, 2018 | Nov. 14, 2018 | Consented | blood | 3 | all-purposes |

It is notable that the report in Table 1 does not include any PII such as names, phone numbers, emails, etc. While the inventive system collects, stores, and encrypts this information it strictly restricts access to it.

After patient's consent, the biological sample/specimen is taken and may be associated with an identifier that uniquely associate the sample with the patient's ICF document. When the code is read, e.g., by scanning, the inventive system may instantly, without a person having to determine the patient's identity and read the full-text of their signed ICF documents, return attributes of the patient's ICF document, even when the patient has updated some or all of the attributes.

Figure 3:
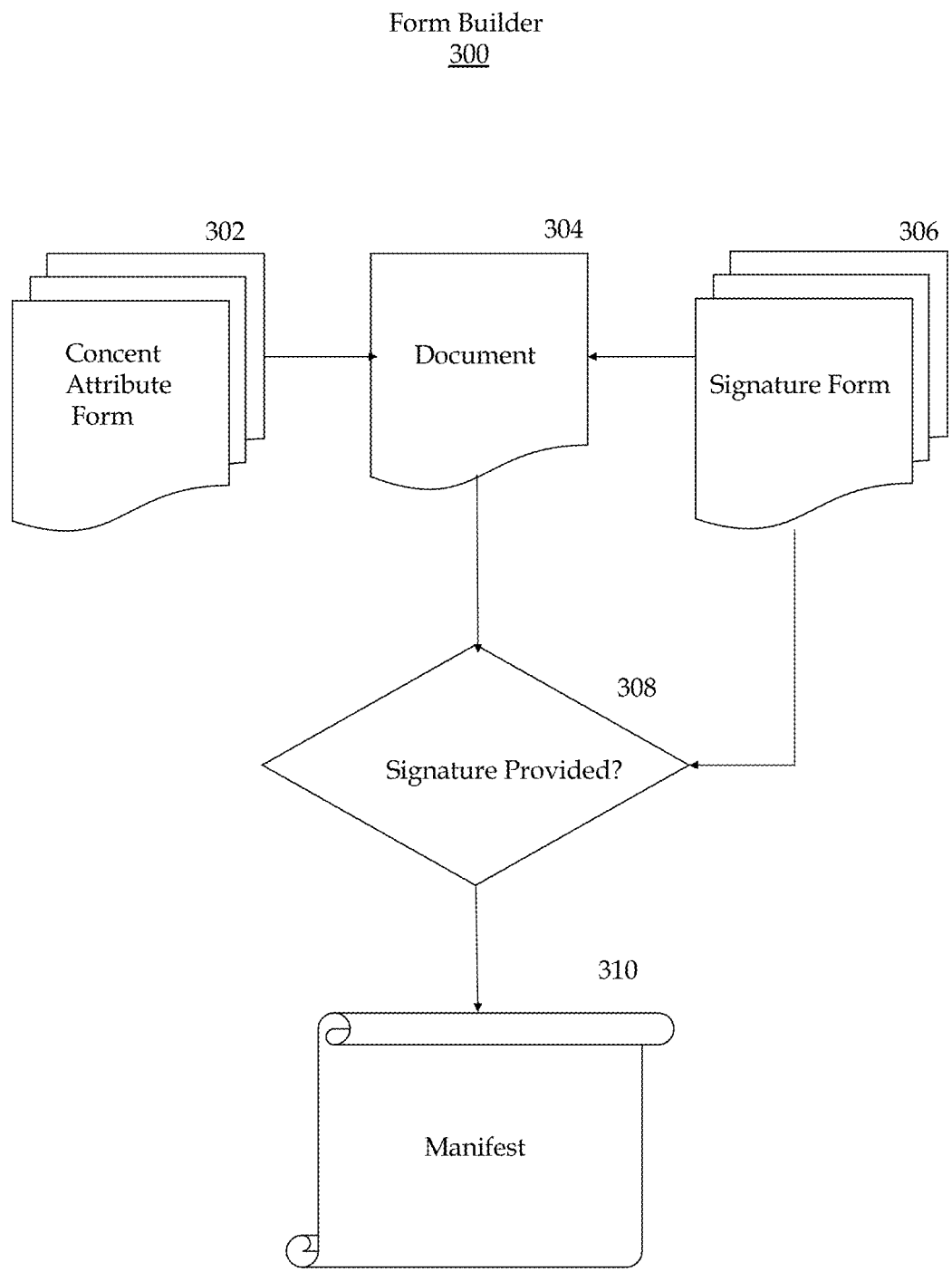
FIG. 3 is a flowchart illustrating creation of an executed manifest in accordance with an embodiment of the present inventive system.

FIG. 3 offers another look at the creation of an executed manifest 310 using the form-builder application 300 of an embodiment of the present inventive system. To generate manifest 310, ICF document 304 is created by a user, e.g., an administrator using the application to create consent attribute forms 302 describing the attributes of the biological sample/specimen and the attributes of the envisioned clinical research or studies for which the biological sample/specimen will be taken.

Further, the user forms signature forms 306 to be associated with the formed consent attribute forms 302. The formed consent attribute forms 302 and the signature forms 306 are then combined to build the unexecuted ICF document 304 which can be presented or forwarded via a network to the patient for signature.

After verifying, at step 308, that the patient has approved of the provisions stipulated to in the consent attribute forms 302 by providing the signature or signing signature forms 306, form builder creates manifest 310 to include the attributes and the metadata associated with the attributes, as well as a version number. The version number is assigned to indicate uniqueness of the attributes. The assigned version number changes when the attributes change, as for example when the patient withdraws consent, gives consent to additional provisions of ICF document 304 or when metadata, i.e., descriptions associated with the clinical research or studies are added or modified.

Thus, for example, consent attribute forms 302 may include metadata fields requesting permission to draw blood; to reuse the sample; and what duration to store the sample. The respective attributes may be yes; yes; 15 years. Similarly, signature forms 306 may include metadata fields asking patients' permission to notify primary care physician; to sequence the patient's genome; and to use the information for reproductive research. The respective attributes may be, no; no; and yes. Manifest 31 based on the described consent attribute forms 302 and signature forms 306, may be shown as follows:

```
"attributes": {
    "sample-reuse": "true",           - Sample reuse: yes
    "sample-type": "blood",           - Blood draw: yes
    "storage-duration-years": "15",   - Storage duration: 15 years
    "notify-primary-care": "false",   - Notify primary care: no
    "sequence-genome": "false",       - Sequence genome: no
    "reproductive-research": "true"   - Use for reproductive research:
                                        yes
}
```

Figure 4:
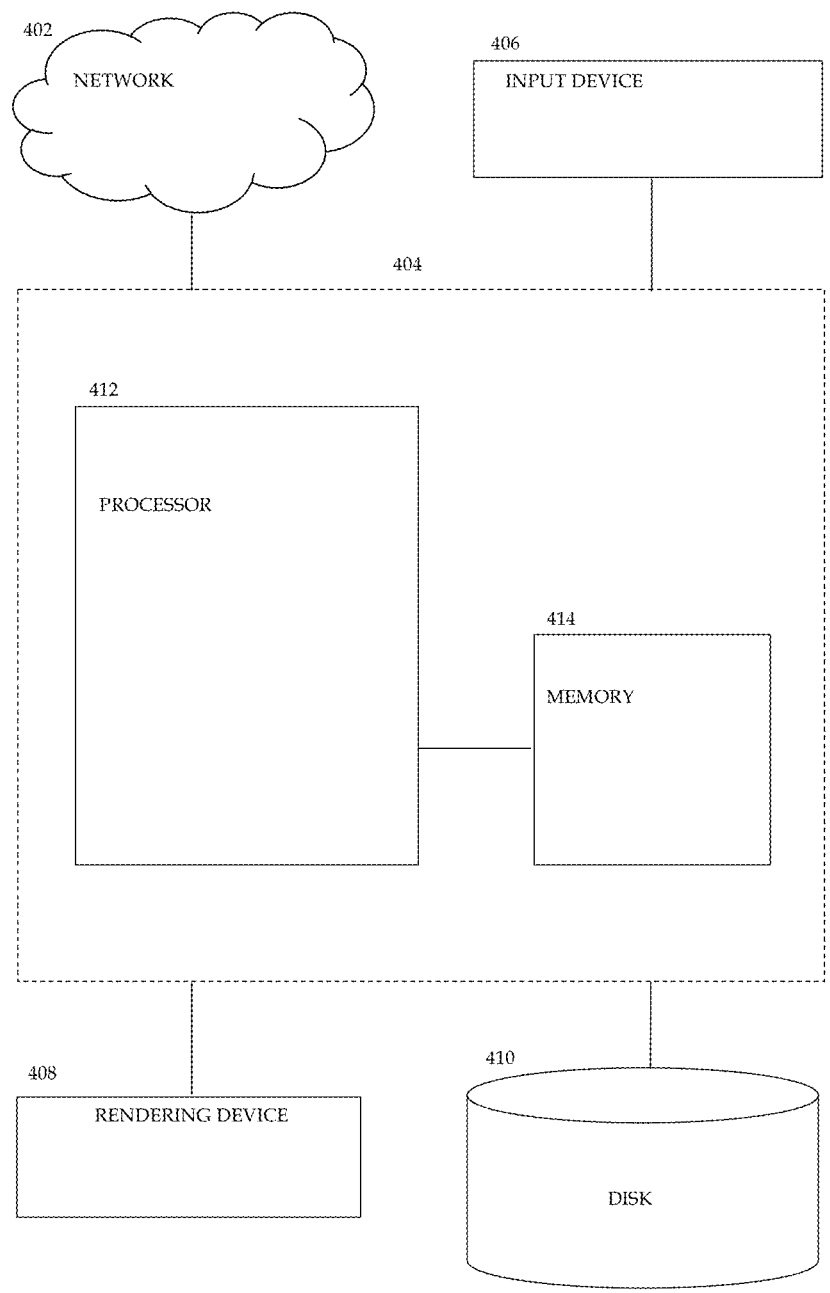
FIG. 4 is a diagram illustrating an example of a digital communication device in accordance with the embodiment of the present inventive system.

Finally, FIG. 4 shows a system 400 which represents an example of computing device 404 utilized to implement the form-builder application 300 (the present inventive system described above as well as any digital communication devices that may be used in conjunction with the computing device. The system 400 includes computing device 404 that has processor 412 operationally coupled to one or more of: units of memory 414; rendering devices 408, such as one or more of a display, speaker, printer, transceiver, etc.; peripheral input devices 406; and network 402 operationally coupled to computing device 404.

Any external content may be received by processor 412 and is used to perform operations in accordance with the present inventive system. The operations may include controlling rendering device 408 to render, e.g., a user interface (UI) and/or content in accordance with the present inventive system as illustrated in the Figs.

Input device 406 may include one or more computer keyboard, a pointing device, e.g., a computer mouse, a microphone, touch sensitive displays screens, which may be stand alone or be a part of rendering device 408. User input device 406 is operable to interact with processor 412 including interaction within a paradigm of the UI and/or other elements of the present inventive system, such as to enable web browsing, content selection, such as provided by left and right clicking on a device, a mouse-over, pop-up menu, radio button, etc., such as provided by user interaction with a computer mouse, etc., as may be readily appreciated by a person of ordinary skill in the art.

In accordance with an embodiment of the present inventive system, rendering device 408 may operate as a touch sensitive display for communicating with processors 412, and thereby, rendering device 408 may also operate as input device 406. In this way, a user may interact with processor 412. Clearly user device 404, processor 412, memory 414, rendering device 408, optional disk 410 and/or user input device 406 may all or partly be portions of a computer system or other device, and/or be embedded in a portable device, such as a mobile device, personal computer, tablet, personal digital assistant, converged device such as a smart telephone, etc.

The methods of the present inventive system are particularly suited to be carried out by a computer software program, such program containing modules corresponding to one or more of the individual steps or acts described and/or envisioned by the present inventive system. Such program may of course be embodied in a computer-readable medium, such as an integrated chip, a peripheral device or memory, such as memory 414 and/or other memory devices coupled to processor 412.

The computer-readable medium and/or memory 414 may be any recordable medium (e.g., random access memory, read only memory, removable memory, memory cards, compact discs, and digital optical disk storage, hard drives, floppy disks) or may be a transmission medium utilizing one or more of radio frequency coupling, Bluetooth coupling, infrared coupling etc. Any medium known or developed that may store and/or transmit information suitable for use with a computer system may be used as the computer-readable medium and/or memory 414.

Additional memories may also be used. The computer-readable medium, memory 414, and/or any other memories may be long-term, short-term, or a combination of long-term and short-term memories. These memories configure processor 412 to implement the methods, operational acts, and functions disclosed herein. The operation acts may include controlling rendering device 408 to render elements in a form of the UI and/or controlling rendering device 408 to render other information in accordance with the present inventive system. The memories may be implemented as electrical, magnetic or optical memory, or any combination of these or other types of storage devices.

Network 402 should be understood to include further network connections to other user devices, systems (e.g., servers), etc. While not shown for purposes of simplifying the following description, it is readily appreciated that network 402 may include an operable interconnection between processors, memories, displays and user inputs similar as shown for user device 404, as well as networked servers, such as may host websites, etc. Accordingly, while the description contained herein focuses on details of interaction within components of user device 404 and other user devices and servers, it should be understood to similarly apply to interactions of other devices operably coupled to network 402.

Processor 412 is capable of providing control signals and/or performing operations in response to input signals from the user input device 406 and executing instructions stored in memory 414 or on disk 410. Processor 412 may be an application-specific or general-use integrated circuit(s). Further, processor 412 may be a dedicated processor for performing in accordance with the present inventive system or may be a general-purpose processor wherein only one of many functions operates for performing in accordance with the present inventive system. Processor 412 may operate utilizing a program portion, multiple program segments, or may be a hardware device utilizing a dedicated or multi-purpose integrated circuit.

Thus, while the present inventive system has been described with reference to exemplary embodiments, it should also be appreciated that numerous modifications and alternative embodiments may be devised by those having ordinary skill in the art without departing from the broader and intended spirit and scope of the present inventive system as set forth in the claims that follow.

The section headings included herein are intended to facilitate a review but are not intended to limit the scope of the present inventive system. Accordingly, the specification and drawings are to be regarded in an illustrative manner and are not intended to limit the scope of the appended claims.

What is claimed is:

1. A computing-device implemented method, comprising:
   presenting user-selectable attributes and user-selectable data fields to an administrator;
   constructing an informed consent form (ICF) for participants of a medical study based on a first set of selections of the administrator;
   receiving consent to the ICF from the participants of the medical study, wherein the ICF includes attributes of the medical study;
   generating a record for each participant, wherein each record includes an identifier of the participant, the attributes of the ICF, and a version identifier that is unique to the ICF;
   constructing a modified ICF based on a second set of selections of the administrator;
   receiving consent to the modified ICF from one or more of the participants, wherein the modified ICF includes a modified attribute;
   updating the records of the one or more participants for whom consent to the modified ICF is received to reflect the modified attribute and a version identifier that is unique to the modified ICF; and
   generating a report based on the records of the participants from the medical study, wherein the report includes the participant identifiers and attributes for which the respective participants have consented.

2. The method of claim 1, wherein the report further includes:
   consent statuses of the respective participants.

3. The method of claim 2, wherein the consent statuses are based on the version identifiers of the ICFs to which the respective participants consented.

4. The method of claim 1, further comprising:
   constructing a second ICF for a second medical study based on a third set of selections of the administrator;
   wherein the generating a report comprises generating the report based on records of participants of the medical study and participants of the second medical study.

5. The method of claim 1, further comprising:
   associating a scannable code with each of the participants; and
   associating the scannable codes with biological samples of the respective participants.

6. The method of claim 1, further comprising:
   receiving a code from a code scanning device; and
   retrieving the record of one of the participants based on the code.

7. The method of claim 1, further comprising:
   searching the records to identify participants who have not consented to the modified ICF;
   searching the records to determine uses of biological specimens for which respective participants have consented; and/or
   searching the records to identify biological specimens for which a desired use is permitted.

8. The method of claim 1, wherein the attributes include attributes related to collection, use, and/or disposition of biological samples of the participants.

9. The method of claim 1, wherein the ICF further includes data fields to capture personal information of the participants.

10. The method of claim 1, wherein the attributes include a type of biological specimen of the medical study.

11. The method of claim 10, wherein the attributes include at least one of a blood type, genome sequence, or sample of blood.

12. A non-transitory computer readable media encoded with a computer program that comprises instructions to cause a processor to:
   present user-selectable attributes and user-selectable data fields to an administrator;
   construct an informed consent form (ICF) for participants of a medical study based on a first set of selections of the administrator;
   receive consent to the ICF from the participants of the medical study, wherein the ICF includes attributes of the medical study;
   generate a record for each participant, wherein each record includes an identifier of the participant, the attributes of the ICF, and a version identifier that is unique to the ICF;
   construct a modified ICF based on a second set of selections of the administrator;
   receive consent to the modified ICF from one or more of the participants, wherein the modified ICF includes a modified attribute;
   update the records of the one or more participants for whom consent to the modified ICF is received to reflect the modified attribute and a version identifier that is unique to the modified ICF; and
   generate a report based on the records of the participants from the medical study, wherein the report includes the participant identifiers and attributes for which the respective participants have consented.

13. The non-transitory computer readable media of claim 12, wherein the report further includes:
consent statuses of the respective participants.

14. The non-transitory computer readable media of claim 13, wherein the consent statuses are based on the version identifiers of the ICFs to which the respective participants consented.

15. The non-transitory computer readable media of claim 12, further comprising instructions to cause the processor to:
construct a second ICF for a second medical study based on a third set of selections of the administrator; and
generate the report based on records of participants of the medical study and participants of the second medical study.

16. The non-transitory computer readable media of claim 12, further comprising instructions to cause the processor to:
associate a scannable code with each of the participants; and
associate the scannable codes with biological samples of the respective participants.

17. The non-transitory computer readable media of claim 12, further comprising instructions to cause the processor to:
receive a code from a code scanning device; and
retrieve the record of one of the participants based on the code.

18. The non-transitory computer readable media of claim 12, further comprising instructions to cause the processor to:
search the records to identify participants who have not consented to the modified ICF;
search the records to determine uses of biological specimens for which respective participants have consented; and/or
search the records to identify biological specimens for which a desired use is permitted.

19. The non-transitory computer readable media of claim 12, wherein the attributes include attributes related to collection, use, and/or disposition of biological samples of the participants.

20. The non-transitory computer readable media of claim 12, wherein the ICF further includes data fields to capture personal information of the participants.

* * * * *